United States Patent
St. Cyr et al.

(10) Patent No.: US 6,692,473 B2
(45) Date of Patent: Feb. 17, 2004

(54) DUAL LUMEN ADJUSTABLE LENGTH CANNULAE FOR LIQUID PERFUSION OR LAVAGE

(76) Inventors: John A. St. Cyr, 12683 Drake St. NW., Coon Rapids, MN (US) 55448; J. Michael Holton, 1007 Lantern Hill Ct., Salisbury, MD (US) 21804; Theodore C. Kelly, 4515 Saddlewood Dr., Minnetonka, MN (US) 55345; Linda M. Shecterle, 940 Fernbrook La. North, Plymouth, MN (US) 55447

( * ) Notice: Subject to any disclaimer, the term of this patent is extended or adjusted under 35 U.S.C. 154(b) by 146 days.

(21) Appl. No.: 09/863,230

(22) Filed: May 24, 2001

(65) Prior Publication Data

US 2002/0177822 A1 Nov. 28, 2002

(51) Int. Cl.$^7$ .......................... A61M 25/00; A61M 5/00
(52) U.S. Cl. ................................ 604/264
(58) Field of Search .................. 604/269, 45, 263, 604/164.02, 181, 264, 43

(56) References Cited

U.S. PATENT DOCUMENTS 4,531,935 A * 7/1985 Berryessa .................. 604/45

* cited by examiner

*Primary Examiner*—Henry Bennett
*Assistant Examiner*—Sabrina Dagostino
(74) *Attorney, Agent, or Firm*—Kathleen R. Terry

(57) ABSTRACT

The invention is a dual lumen, adjustable cannula assembly which comprises an inner cannula which is moveable within an outer cannula. Each cannula has openings for fluid passage. The assembly may be placed at any region within a body cavity such as the peritoneal cavity, the vena cava, veins or arteries. The inner cannula can be advanced beyond the position of the cannula assembly so as to communicate with a region of the cavity different from that with which the outer cavity communicates.

15 Claims, 6 Drawing Sheets

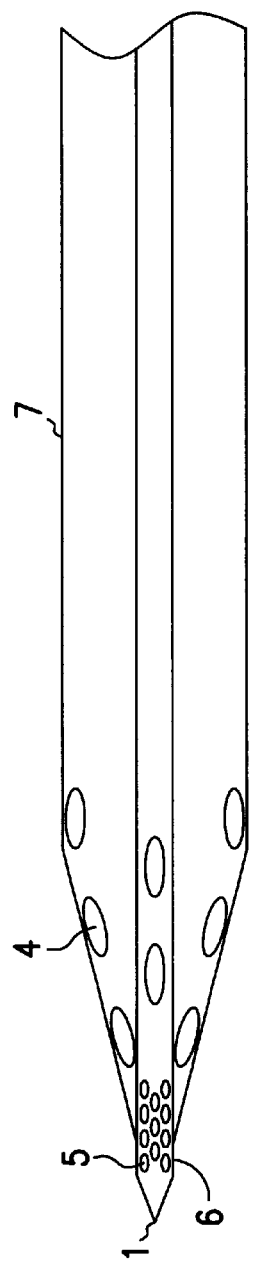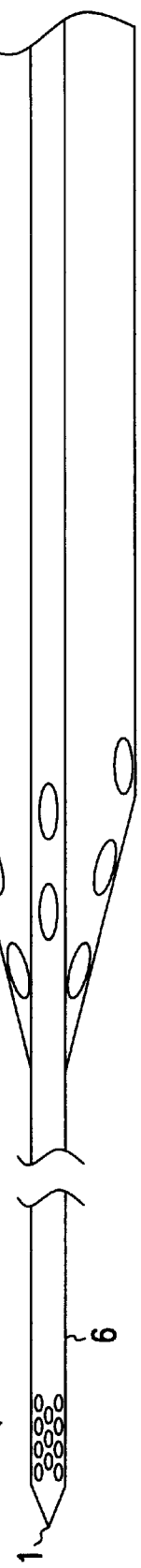

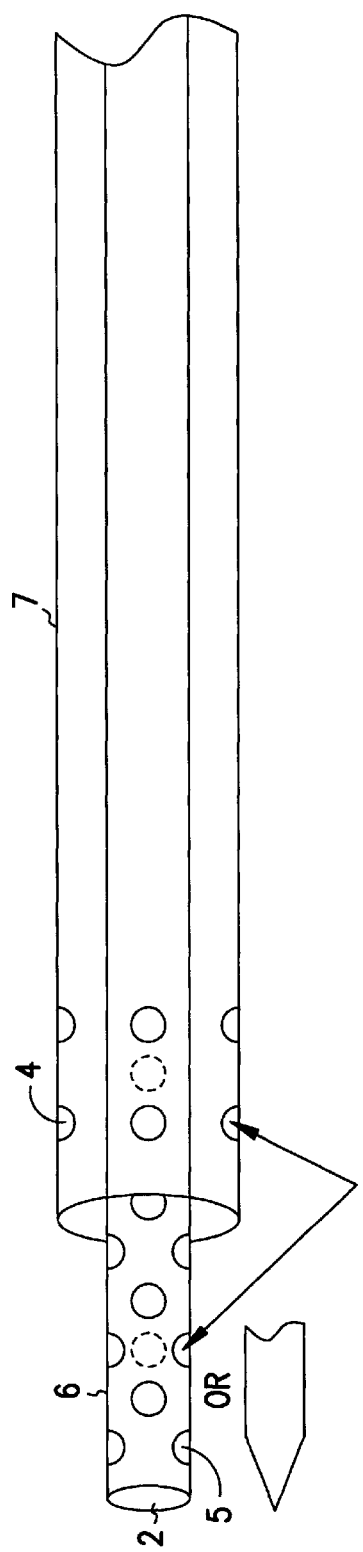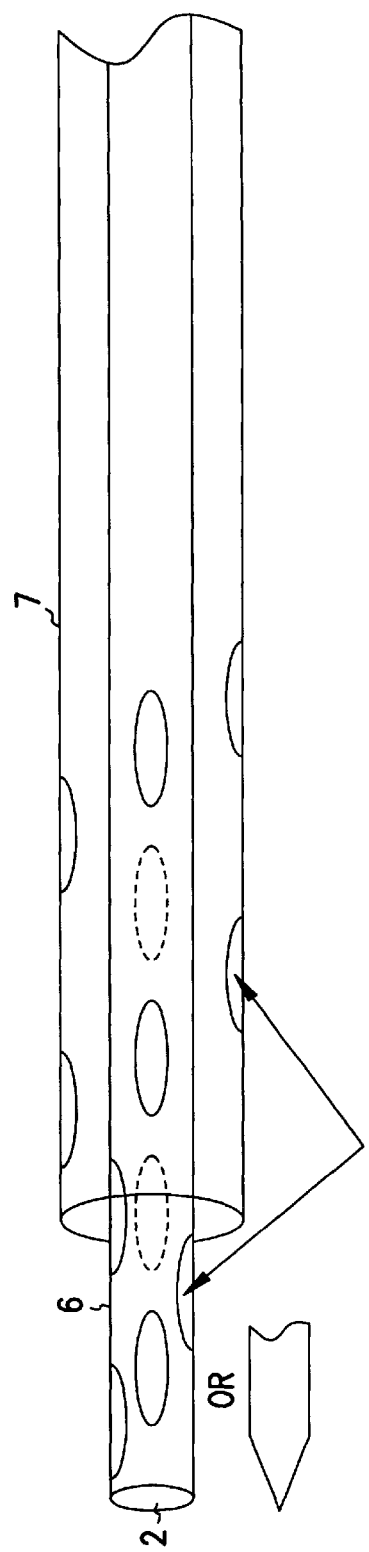

DUAL LUMEN ADJUSTABLE LENGTH CANNULAE FOR LIQUID PERFUSION OR LAVAGE

FIELD OF THE INVENTION

This invention relates to cannulae for the introduction and withdrawal of fluids from body cavities such as the peritoneum, vena cava, veins, arteries, heart chambers.

BACKGROUND OF THE INVENTION

Introduction of tubing for the introduction and withdrawal of fluids from body cavities is well known. Generally, such tubing is termed a cannula or a catheter. An example of the use of a cannula for diagnostic purposes is the determination of blood flow by infusing a dye, allowing dilution and withdrawing a sample. An example of the use of a cannula for therapeutic purposes is the placement of an indwelling catheter connected to an insulin pump. In most procedures, introduction of the cannula is percutaneous or under indirect visualization. A small incision can be made for the insertion of the cannula. For purposes such as those, a single cannula may suffice. For certain procedures, it is desirable to have different channels of introduction and withdrawal to avoid contamination of one fluid with the other, or to allow simultaneous introduction and withdrawal of fluids. Two cannulas may be inserted, but such a procedure would require two incisions and possibly two technicians to monitor and coordinate introduction and withdrawal of fluids; and furthermore, an appreciable distance may be required for optimal efficiacy.

U.S. Pat. No. 4,755,176 discloses a double lumen cannula, with side holes in the outer wall communicating with the vessel in which it is placed. Fluid may be introduced through the tip of the minor lumen, while fluid in the vessel, which has entered through the side holes, may be withdrawn through the outer lumen.

However, a need exists for a dual lumen, adjustable cannula in which the inlet and outlet areas have a separated distance.

SUMMARY OF THE INVENTION

The present invention comprises a larger diameter outer cannula with a major lumen, within which resides a fully adjustable smaller diameter inner cannula with a minor lumen, forming a dual cannulae assembly. The inner cannula is of a greater length than the outer cannula and can be advanced within the major lumen to any length necessary to adjust to patient size and vessel length or desired chamber, or to separate the areas of introduction and withdrawal of fluids as required by the procedure. The ability to adjust fully overcomes the current problem of creating an undesirable flow loop with concomitant decreases in efficacy as occurs in a dual lumen cannula that is not adjustable. Each of the lumens is provided with at least one opening at its distal end, which may be at the tip of the cannula but preferably is located on the side wall. Most preferably, each cannula is provided with a plurality of openings placed around the periphery of the cannulae. The cannula assembly may also be fitted with a guide wire to ease insertion. The cannula assembly is inserted percutaneously through a single incision while in the rest position, that is, with the distal ends of the inner and outer cannulae at the same position. Once into the desired body cavity, both are advanced together to the desired area and the inner cannula is then advanced to a farther position as determined by the procedure. Each lumen communicates with a separate external reservoir(s) through a bifurcated joint at the proximal end, which may be fitted with clips, injection ports and the like. The body cavity may be a blood vessel, chamber, i.e. heart, or the peritoneum

DESCRIPTION OF THE DRAWINGS

FIG. 1 shows tip designs useful in the practice of this invention. FIG. 1(a) shows holes (4, 5) in the walls of the inner cannula (6) and outer cannula (7), respectively. FIG. 1(b) shows the inner cannula advanced beyond the outer cannula. FIG. 1(c) shows a cutaway view of the two lumens, with circular openings (4,5). FIG. 1(d) shows a cutaway view of the two lumens with elliptical openings. The tip is tapered (1) or non-tapered (2) or a combination of an non-tapered outer tip (2) and a tapered inner tip (3).

DETAILED DESCRIPTION OF THE INVENTION

The invention is useful wherever fluids are introduced or withdrawn from a body cavity under direct visualization or percutaneously placement. Although it is proposed that in most procedures the inner cannula will communicate with a reservoir containing fluid to be introduced into the cavity and the outer cannula will communicate with a reservoir to receive withdrawn fluid, either can be used in either way. Nor is it necessary that the procedure call for introduction and withdrawal of the fluids. In the case of cardiac surgery, venous blood must be drawn rapidly from the vena cava and ventricular chambers. In that case, both cannulae can be used for withdrawal of fluid. Conversely, when it is necessary to infuse large quantities of fluid, as in replacing blood lost to hemorrhage, the invention can be used to infuse blood at two different locations along the same vessel or chamber.

The dimensions of the cannulae can be adjusted to the procedure. Generally, for ease of operation, the inner cannula will be of a diameter so that it can be easily moved inside the outer cannula. Any material can be used for the tubing. Polyethylene is the preferred material for its flexibility and smoothness, but other materials such as silicone or rubber may be used. Likewise, the size of the cannulae can be varied to fit the procedure and the size of the patient. Cannulae for arterial insertion are generally smaller than those for venous insertion, while peritoneal lavage, including dialysis, advantageously accommodates large cannulae. Among the procedures contemplated for uses of this invention are: veno-venous circuit, as in hyperthermia; venous drainage for cardiac bypass surgery; plasmaphoresis; lavage, including dialysis; unloading of left ventricle; withdrawal of blood to a reservoir, mixing with medications with subsequent infusion; and high dose chemotherapy to tumors.

Figure 2:
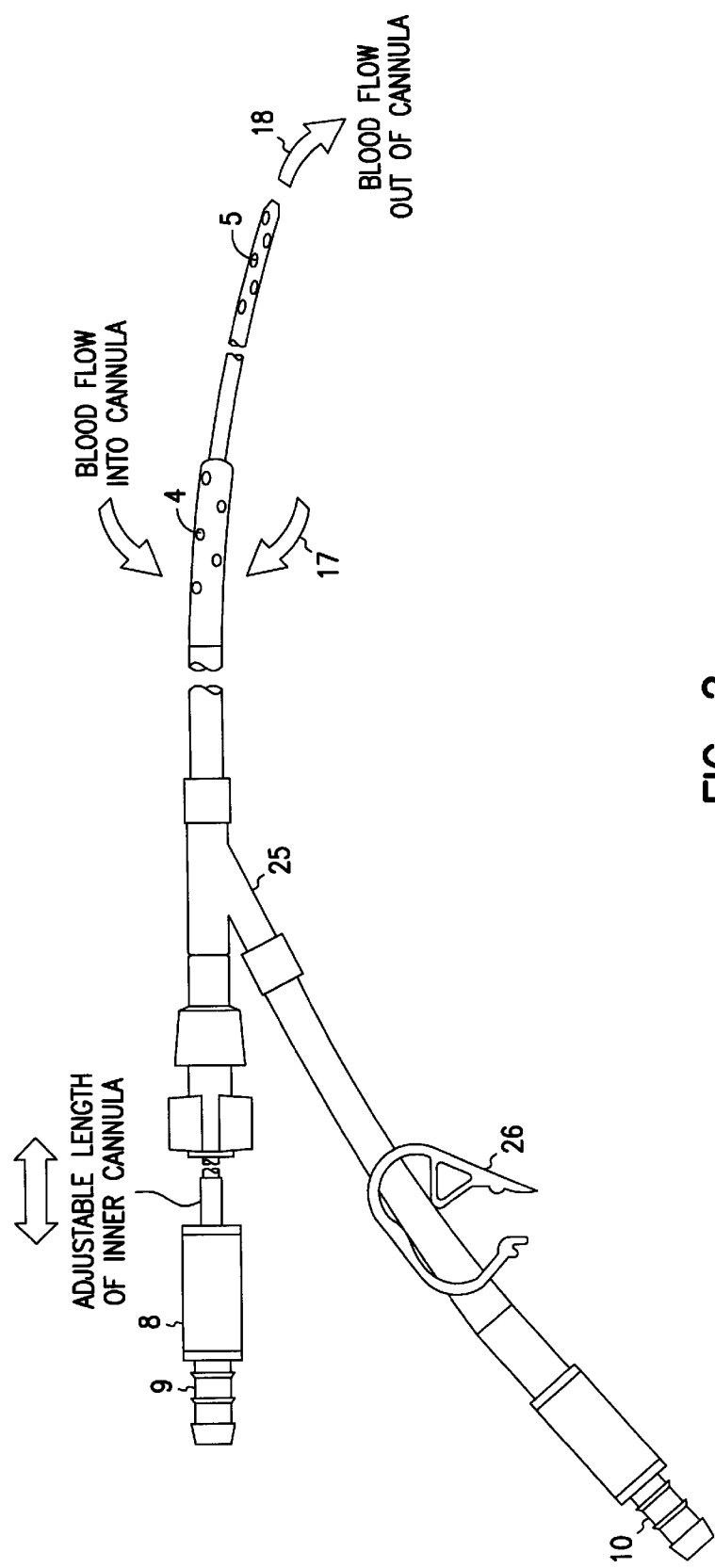
FIG. 2 shows an embodiment of the invention suitable for use in establishing a veno-venous bypass circulation, as in hemodialysis. The outer cannula (4) and inner cannula (5) are cylindrical and hollow. The inner cannula comprises an adjustable screw T-B (8). The outer cannula has a port (10) for the circuit connection, and perforations (4) in its distal end, that is, the end which is inserted into the cavity. The inner cannula has a port (9) and perforations (5) in its distal end. Blood or liquid flow through these perforations can be afferent (17) or efferent (18). A permanent self attached occluding clamp (26) is present at the proximal end of the outer cannula. The cannulae are joined at a "Y" configuration (25), so that while the distal ends are one within the other, the proximal ends, that is, the ends that remain outside the cavity, receive separate reservoirs.
Figure 3:
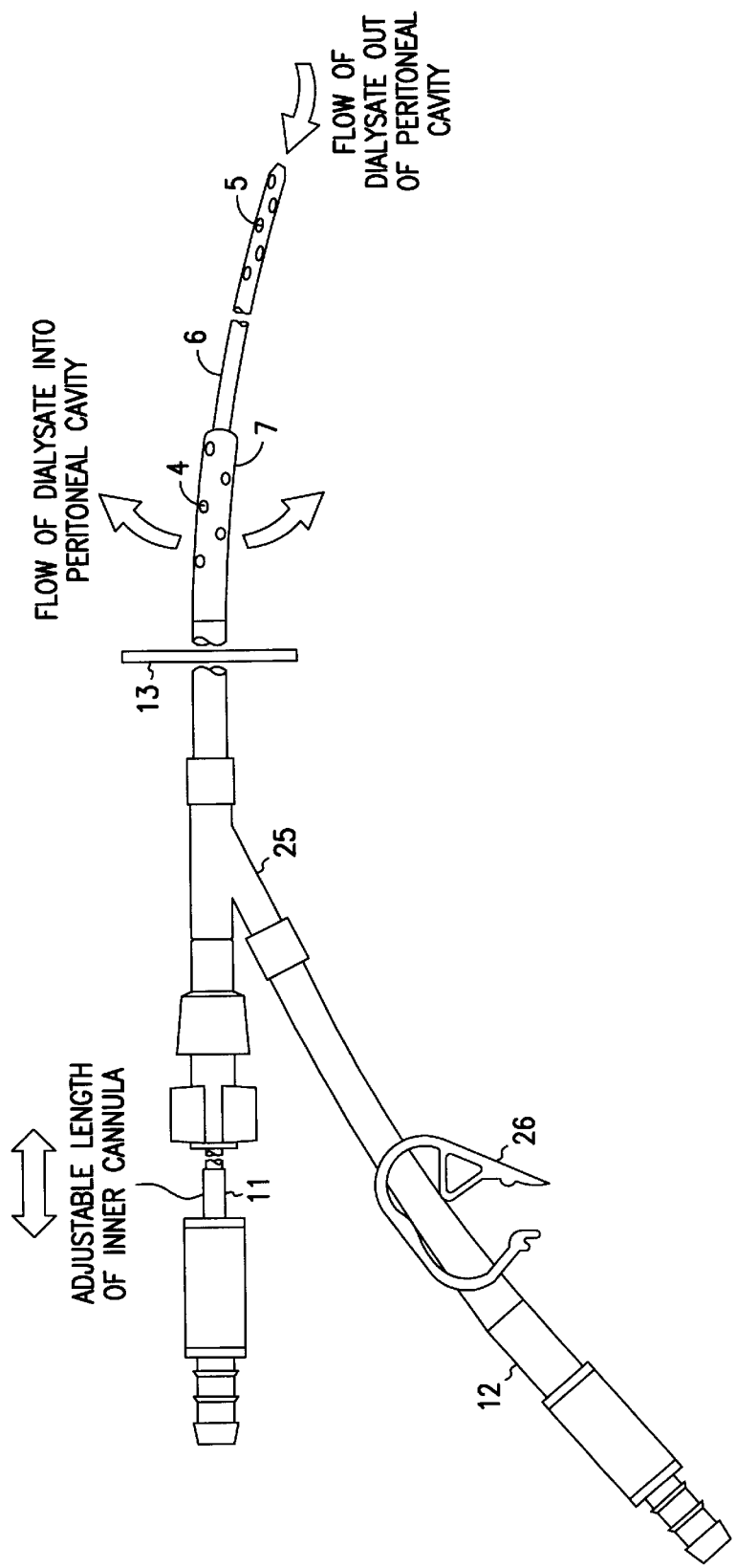
FIG. 3 shows an embodiment suitable for peritoneal lavage, including dialysis. The assembly has been modified for the purpose by providing a flange (13) circumventing both cannulae. The outer cannula (7) and inner cannula (6) are provided with circular (4) or elliptical (5) perforations and the cannulae are surrounded by a flange (13). The exterior ports (11,12) are exterior to the skin of the anterior abdominal wall, with the flange (13) residing in the subcutaneous fat layer. The interior ports (6,7) are positioned within the peritoneum, in which the inner adjustable cannula (6) can be positioned to achieve an ideal placement.
Figure 4:
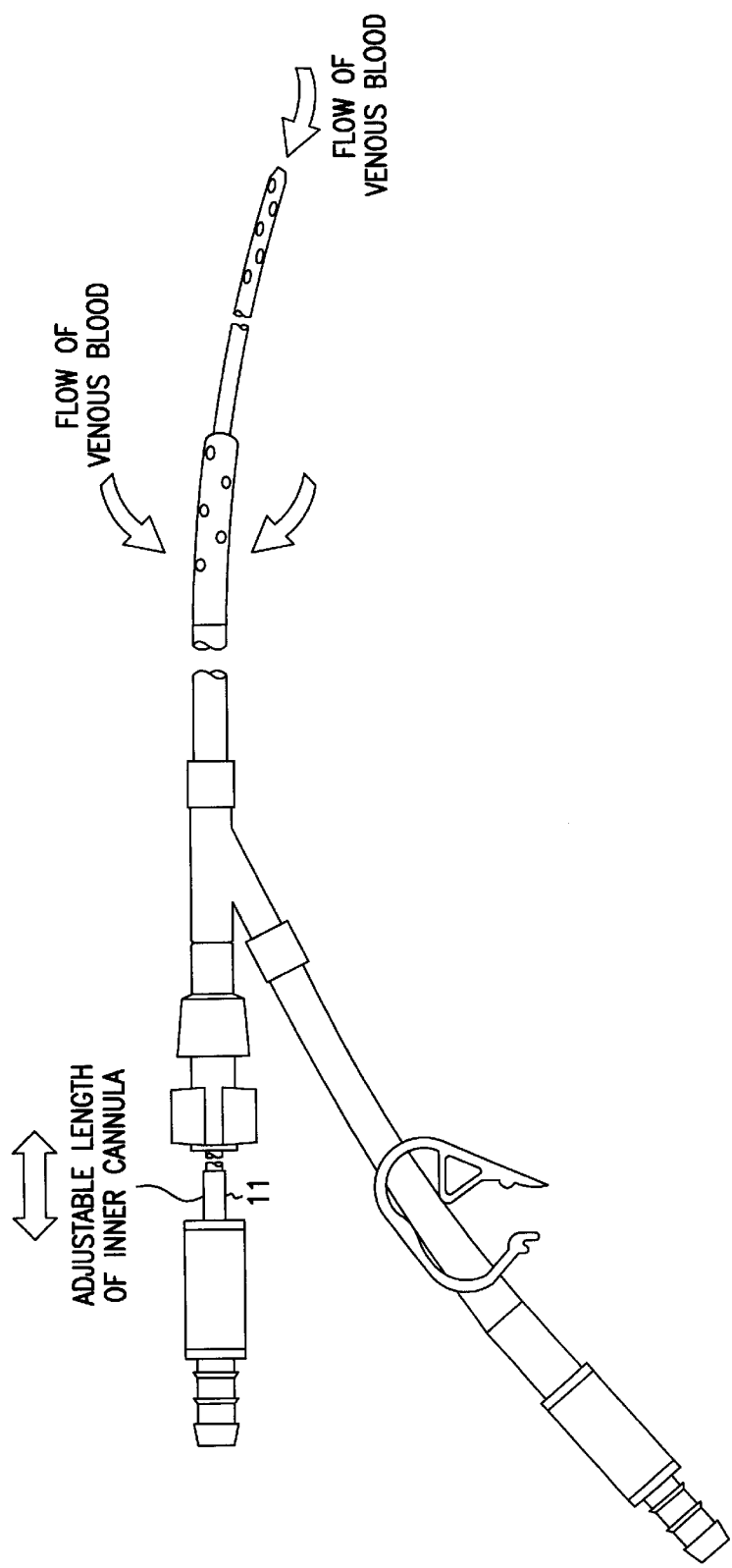
FIG. 4 shows the cannulae of this invention configured for cardiopulmonary bypass procedures.

The present invention comprises an adjustable telescopic dual stage, elongated cannulae, which can be placed percutaneously or under direct vision, following a cutdown procedure. The length of the cannulae assembly can be of various dimensions, depending upon the chosen insertion site and the final position of the each cannula. As shown in FIG. 2, the inner cannula (5) has the capability to be advanced to various lengths, as controlled by the adjustable screw-type mechanism, T-B (8), to secure the desired length of the inner cannula once the appropriate length has been chosen. The distal perforations in each cannulae can be round, elliptical or both and can vary in number from one to about twenty. The perforation can be in the tip of each cannula but more preferably a plurality of perforations are placed in the side walls of the cannulae and at the tip.

EXAMPLE 1
Hemodialysis

For use in hemodialysis, the cannula assembly is introduced into a blood vessel of convenient size. Most patients undergoing chronic dialysis will have had a permanent port installed in a blood vessel, through which the cannula assembly of this invention can be inserted. Hemodialysis may be chronic, as in patients having poor kidney function, or acute. Acute dialysis is often necessary in cases of poisoning and may be combined with antidote therapy or detoxifying procedures. FIG. 2 shows an assembly suitable for venous-venous vascular bypass. The inner cannula is advanced through a region which encompasses an adjustable screw (8) and the length is fixed. Any length that will suffice to avoid a flow loop or "steal concept" is acceptable. The exterior ports are connected to the dialysis machine.

EXAMPLE 2
Peritoneal Lavage, Including Dialysis

Peritoneal lavage, including dialysis, is a procedure in which the peritoneum, a layer lining the abdominal cavity, acts as a dialyzing membrane for the purposes of removing waster products and toxins from the blood of an individual who has acute or chronic renal failure, congestive heart failure, or in individuals with vascular access problems which preclude the use of hemodialysis. The exchange of waste products, such as urea and creatinine, electrolytes or drugs, involves one or more of the following mechanisms: diffusion, osmosis or solvent drag. In diffusion, solutes diffuse from an area of high concentration to a region of lower concentration. Osmosis involves the flow of water molecules or other solvent through a membrane. Intermediate size solutes diffuse by solvent drag, in the which the solute flow rate is increased by a solvent flow in the same direction and decreased with a solvent flow in the opposite direction.

In peritoneal dialysis, chemical and fluid exchange is slow and therefore, causes less stress to the body's internal organs. It also requires no anticoagulants, which are used with hemodialysis; no need for vascular access as in hemodialysis; and requires little other equipment, in contrast to the pumps and membranes that comprise a hemodialysis procedure. Peritoneal dialysis is not recommended for patients with severe abdominal trauma, multiple past surgical procedures, adhesions, severe coagulation defects, paralytic ileus, or previous history of peritonitis.

A patient who is deemed suitable for this procedure, will have a catheter placed, with the tip of the catheter within the peritoneal cavity and the other end (generally a permanent port) outside the body (external). Fluid with desired osmolarity and chemical composition similar to normal body fluid is infused by gravity or by pump into the peritoneal cavity via the permanent catheter, allowed to dwell in the cavity for a period of time and thereafter allowed to drain by gravity or a pump. The osmolarity of the dialysis solution will depend on the therapy. In the case of kidney failure and congestive heart failure, the solution may be somewhat hyperosmolar, in order to remove water from the body.

There are three modes of peritoneal dialysis (1) intermittent peritoneal dialysis; (2) continuous ambulatory peritoneal dialysis; and (3) continuous cycling peritoneal dialysis. In intermittent, the dialysate is introduced, dwells for a short period of time and in then drained. This method is commonly used during the patient's night's sleep. The continuous ambulatory methods consists of instillation of dialysate, dwelling for 4–8 hours, drainage and repeat of the cycle. The continuous cycle method requires a cycle for automatic exchange while the patient sleeps. The last exchange before dawn is allowed to dwell for the entire day. Peritoneal dialysis can cause some potential complications. Obviously, peritonitis is one such complication, which can be due to any contamination to the system. Inefficient dialysis can occur due to catheter site leakage or collusion or blockage of the perforations in the catheter tip which resides within the peritoneal cavity. Respiratory compromise can occur due to fluid retention with excess fluid in the abdominal cavity, thereby exerting increased pressure on the diaphragm, compromising pulmonary function.

The present invention greatly increases the efficiency of peritoneal dialysis and can be used with any of the three methods. The inner cannula, through which the dialysate is drained, is placed into the peritoneal cavity from the outer cannula. The dialysate is introduced through the outer cannula, which is inserted in its external port. The fluid necessarily flows over the maximum area of peritoneum before being discharged or withdrawn (inner cannula). If desired, the introduction and drainage may be switched, with the introduction of the dialysate at the port of the inner cannula and the drainage at the port of the outer cannula. The flow can be easily adjusted by raising or lowering the level of the dialysate reservoir, without the use of pumps.

Peritoneal lavage can also be used for alimentation, generally a combined mixture of fatty acids and amino acids, vitamins, carbohydrates, etc. are delivered in a sterile solution into the peritoneal cavity to assist patients who are unable to digest foods through their intestines. In this case, the solution may be flushed to remove excess components after absorption has occurred.

EXAMPLE 3
Unloading the Left Ventricle Following Cardiac Bypass Surgery

Figure 5:
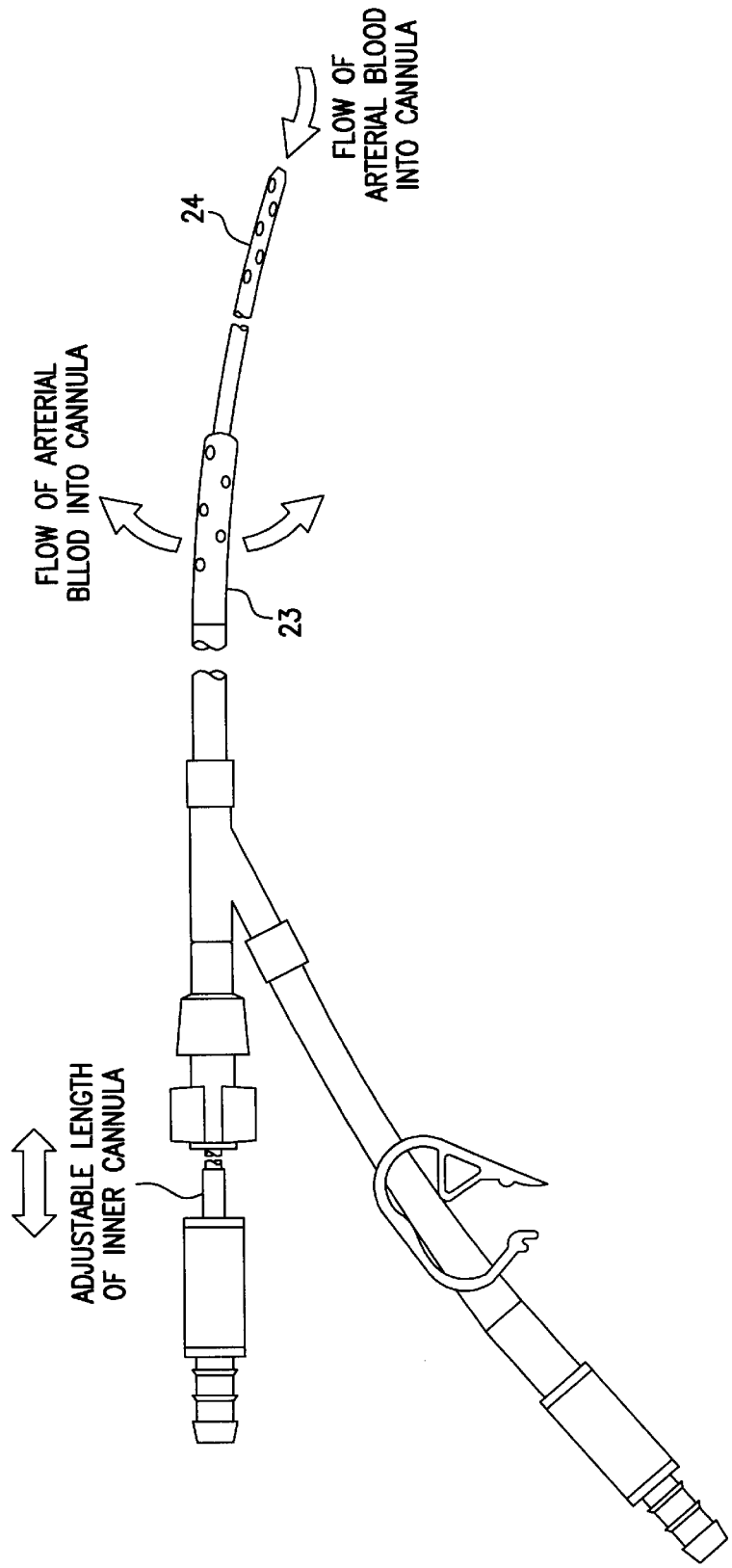
FIG. 5 shows the invention for its use in withdrawing of arterial blood from a chamber (left ventricle) within the heart to aid in the chambers function following cardiac surgery or in certain disease states. Flow is from the inner cannula (24) residing in the left ventricle, to a pumping device and subsequently returning to the aortic outer cannula (23), residing in the aortic root or ascending aorta.

In some patients following cardiac bypass surgery, it is desirable to unload the left ventricle. For this indication, the inner cannula of this invention is advanced so that the tip resides within the left ventricle. As shown in FIG. 5, the blood is drawn into the inner cannula (24) by a pumping device, with return to the aorta cannula placement in the aortic root (23).

EXAMPLE 4
Rapid Volume Expansion

In the case of hemorrhage, large quantities of blood or fluid may need to be added to the circulatory system very quickly. Using this invention, only one cutdown is required to allow infusion at two regions of the body's blood circuit, thereby providing rapid volume replacement without multiple required vascular access sites.

Those skilled in the art may make many modifications and insubstantial changes to the described invention without departing from the spirit and scope of the invention. Therefore, such modifications and variations are considered to be within the scope of the appended claims.

We claim:

1. A dual lumen cannula assembly comprising (a) an outer cannula being provided with a plurality of openings at its distal end; (b) an inner cannula being provided with a plurality of openings at its distal end, said inner cannula being of length greater than that of said outer cannula and placed within and moveable within said outer cannula; and (c) said inner cannular and outer cannula joined through a "Y" shaped joint so that said outer cannula and said inner cannula have separate proximal ends.

2. The dual lumen cannula assembly of claim 1 wherein the plurality of openings at said distal ends are in the side walls of the outer cannula and the inner cannula.

3. The dual lumen cannula assembly of claim 1 wherein the plurality of openings are at the tip of each cannula and in the side walls of the outer cannula and inner cannula.

4. The dual lumen assembly of claim 2 or 3 wherein the openings are round or elliptical.

5. The dual lumen cannula assembly of claim 1 wherein the inner cannula is fitted with a means for limiting its movement.

6. The dual lumen cannula assembly of claim 5 where the means for limiting the movement of the inner cannula is a screw clamp.

7. The dual lumen cannula assembly of claim 1 wherein the distal ends of the outer cannula and the inner cannula are inserted into a blood vessel and the proximal ends of the outer cannula and the inner cannula are in communication with a dialysis machine so that blood is circulated through the dialysis machine and returned to the blood vessel.

8. The dual lumen cannula assembly of claim 7 wherein the distal end of the inner cannula extends farther into the blood vessel, chamber or body region than the distal end of the outer cannula.

9. A dual lumen cannula assembly comprising (a) an outer cannula being provided with an opening at its distal end; (b) an inner cannula being provided with an opening at its distal end, said inner cannula being of length greater than that of said outer cannula and placed within and moveable within said outer cannula; and (c) said inner cannula and outer cannula joined through a "Y" shaped joint so that said outer cannula and said inner cannula have separate proximal ends.

10. A method of using the dual lumen cannula assembly of claim 1 wherein the distal end of the cannula assembly is inserted into a region of a body cavity and the inner cannula is moved within the outer cannula to a region distal to the region in which the outer cannula resides, and the inner cannula is fixed in length and fluid is introduced through one cannula and removed through the other cannula.

11. A method of using the dual lumen cannula assembly of claim 1 wherein the distal end of the cannula assembly is inserted into a blood vessel or body region and the outer cannula resides in a vessel or body region and the inner cannula resides in a vessel, organ chamber or body region at a position distal to the outer cannula.

12. The method of claim 10 wherein the body cavity is a blood vessel.

13. The method of claim 10 wherein the body cavity is an organ chamber.

14. The method of claim 11 wherein the body cavity is a body region.

15. The method of claim 11 wherein the body cavity is the peritoneal cavity.

* * * * *